US006822088B2

(12) United States Patent
Moore et al.

(10) Patent No.: US 6,822,088 B2
(45) Date of Patent: Nov. 23, 2004

(54) SYNTHESIS OF OLIGONUCLEOTIDES ON SOLID SUPPORT

(75) Inventors: Max Moore, Encinitas, CA (US); Achim H. Krotz, San Diego, CA (US); Mark Andrade, Vista, CA (US); Anthony N. Scozzari, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 25 days.

(21) Appl. No.: 10/196,090

(22) Filed: Jul. 16, 2002

(65) Prior Publication Data

US 2003/0032795 A1 Feb. 13, 2003

Related U.S. Application Data

(60) Provisional application No. 60/306,023, filed on Jul. 17, 2001.

(51) Int. Cl.$^7$ ............................................. C07H 21/00
(52) U.S. Cl. ................ 536/25.3; 536/25.31; 536/25.33; 536/25.34
(58) Field of Search ............................. 536/25.3, 25.31, 536/25.33, 25.34

(56) References Cited

U.S. PATENT DOCUMENTS

| | | | |
|---|---|---|---|
| 4,415,732 A | | 11/1983 | Caruthers et al. |
| 4,458,066 A | * | 7/1984 | Caruthers et al. ........ 536/25.34 |
| 4,469,863 A | | 9/1984 | Ts'o et al. |
| 4,476,301 A | | 10/1984 | Imbach et al. |
| 4,500,707 A | | 2/1985 | Caruthers et al. |
| 4,668,777 A | | 5/1987 | Caruthers et al. |
| 4,689,405 A | * | 8/1987 | Frank et al. ............... 536/25.3 |
| 4,725,677 A | | 2/1988 | Köster et al. |
| 4,973,679 A | | 11/1990 | Caruthers et al. |
| 5,023,243 A | | 6/1991 | Tullis ........................ 514/44 |
| 5,037,882 A | * | 8/1991 | Steel ....................... 525/54.11 |
| 5,132,418 A | | 7/1992 | Caruthers et al. |
| RE34,069 E | | 9/1992 | Köster et al. ................. 536/27 |
| 5,175,209 A | * | 12/1992 | Beattie et al. ............ 525/54.11 |
| 5,177,196 A | | 1/1993 | Meyer, Jr. et al. ......... 536/22.1 |
| 5,188,897 A | | 2/1993 | Suhadolnik et al. ...... 428/402.2 |
| 5,194,599 A | | 3/1993 | Froehler et al. .......... 536/26.72 |
| 5,264,423 A | | 11/1993 | Cohen et al. ................. 514/44 |
| 5,276,019 A | | 1/1994 | Cohen et al. ................. 514/44 |
| 5,278,302 A | | 1/1994 | Caruthers et al. ......... 536/24.5 |
| 5,286,717 A | | 2/1994 | Cohen et al. ................. 514/44 |
| 5,321,131 A | | 6/1994 | Agrawal et al. .......... 536/25.32 |
| 5,399,676 A | | 3/1995 | Froehler .................... 536/23.1 |
| 5,405,939 A | | 4/1995 | Suhadolnik et al. ......... 514/44 |
| 5,453,496 A | | 9/1995 | Caruthers et al. ......... 536/24.5 |
| 5,455,233 A | | 10/1995 | Spielvogel et al. ........... 514/44 |
| 5,466,677 A | | 11/1995 | Baxter et al. ................. 514/44 |
| 5,476,925 A | | 12/1995 | Letsinger et al. ......... 536/23.1 |
| 5,519,126 A | | 5/1996 | Hecht ........................ 536/24.3 |
| 5,527,899 A | | 6/1996 | Froehler .................... 536/25.3 |

(List continued on next page.)

FOREIGN PATENT DOCUMENTS

| | | |
|---|---|---|
| WO | 98/39352 | 9/1998 |
| WO | WO 99/11676 A1 * | 3/1999 |
| WO | 99/14226 | 3/1999 |
| WO | WO 00/46281 A2 * | 8/2000 |

OTHER PUBLICATIONS

Mayer et al. (I), "Sampling Characteristics of Octadecylsiloxane–Bonded Silica Particle–Embedded Glass Fiber Discs for Solid Phase Extraction," *Journal of Chromatography A*, 695(2), 267–277 (Mar. 31, 1995).*
Mayer et al. (II), "Retention Characteristics of Octadecylsiloxane–Bonded Silica and Porous Polymer ParticleLoaded Membranes for Solid Phase–Extraction," *Journal of Chromatography A*, 697(1–2), 89–99 (Apr. 21, 1995).*
Kates et al., "Continuous Flow Solid–Phase Peptide Synthesis Using Polystyrene Resins," *Journal of Peptide Research*, 53(6), 682 –683 (1999).*
Kaplan & Itakura, "DNA Synthesis on Solid Supports and Automation," Chapter 2 in *Synthesis and Applications of DNA and RNA*, S. A. Narang (ed.), Academic Press, Inc., New York, NY, 1987, only pp. 9–45 supplied.*
Copy of the PCT International Search Report dated Apr. 22, 2003 (PCT/US02/22739).
Kates, S.A., et al., "Continuous–flow solid–phase peptide synthesis using polystyrene resins," *J. Peptide Res.*, 1999, 63(6) 682–683.
Mayer, M.L., et al., "Sampling characteristics of octadecylsiloxane–bonded silica particle–embedded glass fiber discs for solid–phase extraction," *J. Chromatography A*, 1995, 695, 267–277 (Issue No. 2, Publ. Mar. 31, 1995).
Mayer, M.L., et al., "Retention characteristics of octadecylsiloxane–bonded silica and porous polymer particle–loaded membranes for solid–phase extraction,"*J. Chromatography A*, 1995, 697, 89–99.
Alul, R. H. et al., "Oxalyl–CPG: a labile support for synthesis of sensitive oligonucleotide derivatives," *Nucl. Acid Res.*, 1991, 19, 1527–1532(Apr. 11, 1991).
Brown, T. et al., "Modern machine–aided methods of oligodeoxyribonucleotide synthesis," *Oligonucleotides and Analogues: A Practical Approach*, 1991, Chapter 1, Eckstein, F. (ed.), IRL Press, New York, 1–24.
Wright, P. et al., "Large Scale Synthesis of Oligonucleotides via phosphoramidite Nucleosides and a High–loaded Polystyrene Support," *Tetrahedron Letts.*, 1993, 34, 3373–3376.

Primary Examiner—L. Eric Crane
(74) Attorney, Agent, or Firm—Woodcock Washburn LLP

(57) ABSTRACT

The present invention relates to methods for synthesizing an oligomeric compound on a solid support comprising contacting a solid support with a filling material to produce a mixture thereof; placing the mixture in a reaction vessel; and synthesizing the oligomeric compound. The present invention also relates to (a) reaction vessels for synthesizing oligomeric compounds comprising a solid support; and a filling material, (b) apparatuses for synthesizing oligomeric compounds comprising a reagent source, and a reaction vessel comprising a solid support; and a filling material, and (c) compositions comprising a solid support and a filling material mixed therewith.

28 Claims, 1 Drawing Sheet

U.S. PATENT DOCUMENTS

Figure 1:
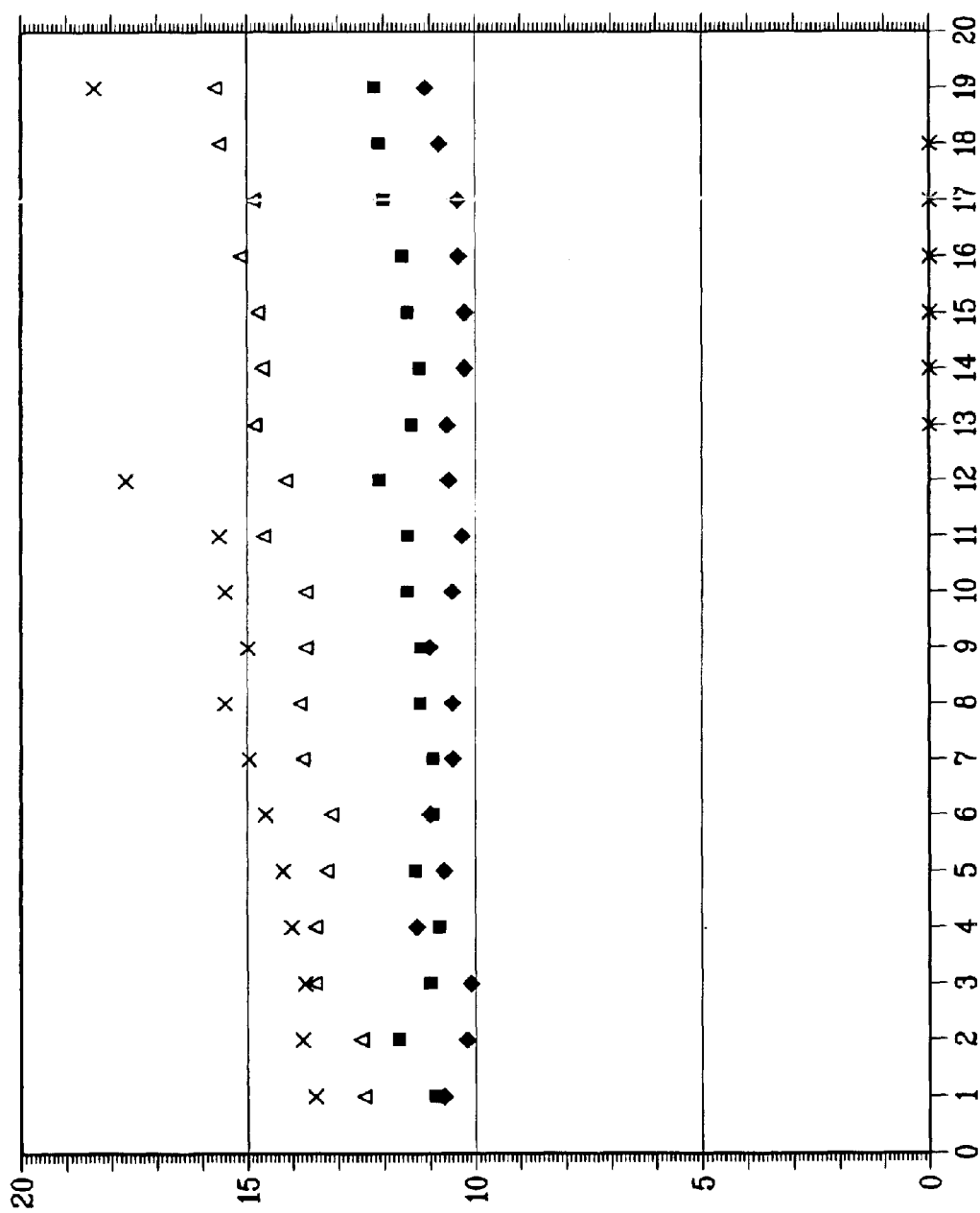

| | | |
|---|---|---|
| 5,536,821 A | 7/1996 | Agrawal et al. ............ 536/22.1 |
| 5,541,306 A | 7/1996 | Agrawal et al. ............ 536/22.1 |
| 5,550,111 A | 8/1996 | Suhadolnik et al. ........... 514/44 |
| 5,563,253 A | 10/1996 | Agrawal et al. ............ 536/22.1 |
| 5,565,555 A | 10/1996 | Froehler et al. ......... 536/26.22 |
| 5,571,799 A | 11/1996 | Tkachuk et al. .............. 514/47 |
| 5,587,361 A | 12/1996 | Cook et al. .................... 514/44 |
| 5,625,050 A | 4/1997 | Beaton et al. ............. 536/24.1 |
| 5,721,218 A | 2/1998 | Froehler ...................... 514/44 |
| 6,121,437 A | 9/2000 | Guzaev et al. ............. 536/26.1 |
| 2003/0032795 A1 * | 2/2003 | Moore et al. ............ 536/25.34 |

* cited by examiner

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tccgtcatcg ctcctcaggg                                                  20
```

SYNTHESIS OF OLIGONUCLEOTIDES ON SOLID SUPPORT

CROSS-REFERENCE TO RELATED APPLICATIONS

This application claims benefit of Provisional Application Ser. No. 60/306,023 filed Jul. 17, 2001, the entirety of which is incorporated herein by reference.

FIELD OF THE INVENTION

This invention relates to methods of synthesizing oligonucleotides and derivatives thereof on solid supports.

BACKGROUND OF THE INVENTION

Oligonucleotides and derivatives thereof are typically prepared through solid phase synthesis regimes performed on solid supports packed in flow-through reactors. Flow-through reactors deliver solvent and reagent to solid supports at a required flow rate. There is an inherent resistance, or back pressure, associated with delivering solvent and or reagent to the solid support. The resistance can be caused by the solvent, the reagent lines, and/or the solid support in the reactor. Back pressure is undesirable because it distorts reaction conditions and makes synthesis techniques less efficient.

The back pressure caused by the solid support depends on the chemical composition of the support. Back pressure is also affected by the physical-chemical characteristics of the support and the packing in the flow through reactor.

The required flow rate of solvents and reagents through a reaction vessel is assured by pumps that overcome back pressure. As back pressure increases, more pumping power is required and modifications to reaction conditions may be necessary. However, pumping power requirements can limit reaction vessel's size or flow-through capacity, and the quality of oligonucleotide synthesized can also be degraded by unfavorable pumping characteristics.

In addition, as oligonucleotide synthesis progresses back pressure increases. If steps are not taken to control the increase in back-pressure before allowed pressure maxima are exceeded, the synthesis cycle has to be modified or otherwise the reaction vessel could become "clogged". Such modifications can include adjusting the flow rate through the reaction vessel or decreasing the size of the reactor.

Low flow rates and smaller reactors are undesirable because of the lower concentration and yields of oligonucleotides that can be synthesized. Similarly, flowrate adjustments during synthesis are undesirable because they are time consuming and may result in inferior oligonucleotide products. Hence, methods which address these needs have long been sought. This invention is directed to these, as well as other, important ends.

SUMMARY OF THE INVENTION

In some embodiments, the invention provides methods for synthesizing an oligomeric compound on a solid support comprising contacting a solid support with a filling material to produce a mixture thereof; placing the mixture in a reaction vessel suitable for use in solid phase synthesis; and synthesizing the oligomeric compound.

In further embodiments, the invention provides reaction vessels for synthesizing oligomeric compounds comprising a solid support; and a filling material.

In further embodiments, the invention provides apparatuses for synthesizing oligomeric compounds comprising a reagent source, and a reaction vessel, said reaction vessel comprising a solid support; and a filling material.

In further embodiments, the invention provides compositions comprising a solid support suitable for oligonucleotide synthesis and a filling material mixed therewith.

In some preferred embodiments of the foregoing methods, apparatuses and compositions, the filling material is glass, preferably glass beads. In further preferred embodiments of the foregoing methods, apparatuses and compositions, the filling material is a polymer, preferably polymeric beads.

In some preferred embodiments of the methods of the invention, the contacting and placing steps occur simultaneously in the reaction vessel. In further preferred embodiments, the oligomeric compound is an oligonucletide, preferably synthesized using phosphoramidite chemistry.

In some preferred embodiments, the filler material is glass, preferably glass beads, and the solid support is a polymer or glass beads, preferably Primer™ 200 support, Tentagel support or POROS support.

In some preferred embodiments, the methods of the invention are used to prepare oligomeric compounds that are oligoncucleotides containing at least one phosphorothioate internucleoside linkage.

DETAILED DESCRIPTION

The present invention provides methods of synthesizing oligonucleotides and derivatives thereof by solid phase synthesis processes that use filling materials to reduce back pressure. In some embodiments, filling materials are mixed with solid supports to reduce back pressure caused by the packing of solid support in a flow through reactor.

The present invention enables oligonucleotide synthesis at higher scales, and at flow rates necessary for the preparation of high quality oligonucleotides. The present methods also significantly reduce, and preferably avoid, flowrate adjustments during synthesis which are time consuming and may result in inferior oligonucleotide product. Also in accordance with the present invention the use of filling materials lowers the back pressure during detritylation and washing steps of synthesis. The use of filling materials in accordance with the present invention also reduces the pressure increase caused by oligomeric compound growth as the synthesis progresses.

As described herein back pressure is the resistance that is experienced by pumps that provide solvent and reagent to a reaction vessel during solid phase synthesis processes. While not wishing to be bound by any particular theory, it is believed that back pressure is caused in part by the packing of the solid support in the flow through reactor, but can also be cause by, for example, the solvent, reagent lines, oligomeric compound growth and/or solid support in the reactor. Back pressure increases as the synthesis progresses.

As described herein filling materials are materials that can be added to solid phase synthesis processes to reduce back pressure. Filling materials can be any inorganic or organic material that is compatible with the conditions of oligonucleotide synthesis, i.e, materials that are substantially inert to the solvents and reagents of the synthesis. Examples of such materials include inorganic materials such as glass and inorganic polymers, organic polymeric materials. Representative examples of polymers that may be used include TentaGel Support—an aminopolyethyleneglycol derivatized support (see, e.g., Wright, et al., *Tetrahedron Letters* 1993, 34, 3373, and Poros—a copolymer of polystyrene/divinylbenzene.

In some preferred embodiments, the filling materials are glass. Types of glass that may be used include controlled pore glass (CPG), and oxalyl-controlled pore glass (see, e.g., Alul, et al., *Nucleic Acids Research* 1991, 19, 1527. However, a wide variety of other glasses can be used in accordance with the invention, as will be apparent to those of skill in the art. In accordance with the present invention, filling materials can have any convenient shape that is amenable to the reduction of back pressure. In some preferred embodiments, the filling material is glass beads.

The filling material can be added to the solid support either in the reactor and mixed therewith, or added to the solid support prior to placing the support in the reactor.

In some embodiments, the ratio of filler material to solid support, on a volume-volume basis can be 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1.

As described herein "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside, or backbone, linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

The present invention is applicable to the preparation of oligonucleotides and analogs thereof. In some embodiments, the methods described herein are used to produce antisense oligonucleotides and other oligonucleotide mimetics such as are described below.

The antisense compounds in accordance with this invention preferably comprise from about 8 to about 50 nucleobases, i.e. from about 8 to about 50 linked nucleosides. Preferred antisense compounds include antisense oligonucleotides. More preferred antisense compounds include antisense oligonucleotides having from about 12 to about 30 nucleobases.

Antisense compounds include ribozymes, external guide sequence (EGS) oligonucleotides (oligozymes), and other short catalytic RNAs or catalytic oligonucleotides which hybridize to the target nucleic acid and modulate its expression.

A nucleoside is a base-sugar combination. In a preferred embodiment the base portion of the nucleoside is a heterocyclic base. The two most common classes of heterocyclic bases are purines and pyrimidines.

Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. When synthesizing oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

The methods of the present invention are employed for use in iterative solid phase oligonucleotide synthetic regimes using any of the wide variety of chemistries known in the art, including, for example, phosphodiester, phosphotriester, H-phosphonate, phosphoramidite chemistries, and other solid phase techniques typically employed for DNA and RNA synthesis. See, e.g., Protocols For Oligonucleotides And Analogs, Agrawal, S., ed., Humana Press, Totowa, N.J., 1993, Crooke, Stanley, Lebleu, Bernard, Antisense Research and Applications, CRC Press, 1993, and F.Eckstein, Oligonucleotides and Analogues, A Practical Approach, Oxford University Press, 1991, and Blackburn, G. M and Giat, M. J., Nucleic Acids in Chemistry and Biology, 2nd Edition, Oxford Univ. Press New York 1996.

A discussion of various types of oligomeric compounds capable of being synthesized by methods of the present invention, and some representative synthetic synthetic chemistries, are described below.

In one embodiment of oligonucleotide synthesis, for example, a nucleoside is anchored to a solid support which is functionalized with hydroxyl or amino residues. Additional nucleosides are subsequently added in a step-wise fashion to form the desired linkages between the functional group of an incoming nucleoside, and a hydroxyl group of the support bound nucleoside. Implicit to this step-wise assembly is the judicious choice of suitable protecting groups. Such protecting groups serve to shield phosphorus moieties of the nucleoside base portion of the growing oligomer until such time that it is cleaved from the solid support.

When cleavage from the support is desired, the support-bound monomer or higher order synthon is then treated to remove the protecting group from the free terminal end. Typically, this is accomplished by treatment with acid. The solid support bound monomer, or higher order oligomer, is then reacted with individual monomeric or higher order building blocks (i.e., synthons) to form a compound which has a phosphite or thiophosphite linkage.

Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069, which are hereby incorporated by reference in its entirety. A linker is optionally positioned between the terminal nucleotide and the solid support. Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Ekstein, F. Ed., IRL Press, N.Y., 1991, Chapter 1.

Solid supports suitable for use in the invention include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al., *Tetrahedron Letters* 1993, 34, 3373, and Poros—a copolymer of polystyrene/divinylbenzene.

In another embodiment, the solid support is derivatized to provide an acid labile trialkoxytrityl group, such as a trimethoxytrityl group (TMT). Without being bound by theory, it is expected that the presence of the trialkoxytrityl protecting group will permit initial detritylation under conditions commonly used on DNA synthesizers. For a faster release of oligonucleotide material in solution with aqueous ammonia, a diglycoate linker is optionally introduced onto the support.

In some preferred embodiments, the methods of the invention are amenable to synthesis oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N$_3$)—(CH$_2$— and —O—N(CH$_3$)—CH$_2$—CH$_2$— [wherein the native phosphodiester backbone is represented as —O—P—O—CH$_2$—] as described in U.S. Pat. No. 5,489,677 which is herein incorporated by reference in its entirety, and the amide backbones as described in U.S. Pat. No. 5,602,240 which is herein incorporated by reference in its entirety. Also preferred are oligonucleotides having morpholino backbone structures as described in U.S. Pat. No. 5,034,506, which is herein incorporated by reference in its entirety.

In another preferred embodiment, synthetic solid phase synthesis processes utilizes phosphoramidites as activated phosphate compounds as disclosed in U.S. Pat. No. 6,121,437 which is herein incorporated by reference. In this technique, a phosphoramidite monomer is reacted with a free hydroxyl on the growing oligomer chain to produce an intermediate phosphite compound, which is subsequently oxidized to the P$^V$ state using standard methods. This technique is commonly used for the synthesis of several types of linkages including phosphodiester, phosphorothioate, and phosphorodithioate linkages.

Typically, the first step in such a process is attachment of a first monomer or higher order subunit containing a protected 5'-hydroxyl to a solid support, usually through a linker, using standard methods and procedures known in the art. The support-bound monomer or higher order first synthon is then treated to remove the 5'-protecting group, to form a compound which has a phosphite or thiophosphite linkage. In preferred embodiments, synthons are reacted under anhydrous conditions in the presence of an activating agent such as, for example, 1H-tetrazole, 5-(4-nitrophenyl)-1H-tetrazole, or diisopropylamino tetrazolide.

In some preferred embodiments, phosphite or thiophosphite compounds containing a linkage are oxidized or sulfurized to produce compounds having a different linkage. Choice of oxidizing or sulfurizing agent will determine whether the linkage will be oxidized or sulfurized to a phosphotriester, thiophosphotriester, or a dithiophosphotriester linkage.

Treatment with an acid removes the 5'-hydroxyl protecting group, and thus transforms the solid support bound oligomer into a further compound, which can then participate in the next synthetic iteration; i.e., which can then be reacted with a further compound. This process is repeated until an oligomer of desired length is produced.

The completed oligomer is then cleaved from the solid support. The cleavage step can precede or follow deprotection of protected functional groups. During cleavage, the linkages between monomeric subunits are converted from phosphotriester, thiophosphotriester, or dithiophosphotriester linkages to phosphodiester, phosphorothioate, or phosphorodithioate linkages. This conversion is effected through the loss of an oxygen or sulfur protecting group.

A wide variety of bases can be used to initiate the removal of the protecting groups of the present invention. These include aqueous ammonium hydroxide, aqueous methylamine, DBU (1,8-diazabicyclo[5.4.0]undec-7-ene) and carbonates containing counterions such as lithium, potassium, sodium, and cesium. Most preferred is potassium carbonate and ammonia. Removal of the protecting groups may be performed in a variety of suitable solvents. These solvents include those known to be suitable for protecting group removal in oligonucleotide synthesis. In the case of ammonia, water is the preferred solvent, whereas when using carbonates, alcohols are preferred. Methanol is most preferred. In certain preferred embodiments, conditions for removal of the oxygen or sulfur protecting group also effect cleavage of the oligomeric compound from the solid support.

The methods of the present invention are amenable to synthesis of any oligomeric compound or any oligonucleotide capable of being synthesized by solid phase synthesis processes. Specific examples of preferred oligomeric compound or oligonucleotide capable of being synthesized by methods of this invention include oligonucleotides containing modified backbones or non-natural internucleoside linkages. As described herein, oligonucleotides having modified backbones include those that retain a phosphorus atom in the backbone and those that do not have a phosphorus atom in the backbone. As described herein, modified oligonucleotides that do not have a phosphorus atom in their internucleoside backbone can also be considered to be oligonucleosides.

Oligomers amendable to preparation by the methods of the invention include those having modified oligonucleotide backbones including, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. In some embodiment's oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, for example, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; and 5,625,050, each of which is herein incorporated by reference in its entirety.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference in its entirety.

Modified oligonucleotides can be prepared using the method of the invention that also can contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples herein, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$, also described in examples herein.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-$OCH_2CH_2CH_2NH_2$), 2'-allyl (2'—$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar.

Representative United States patents that teach the preparation of such modified sugar structures include, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase, often referred to simply as "base", modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines such as phenoxazine cytidine(1H-pyrimido[5,4-b][1,4]benzoxazin-2(3H)-one), phenothiazine cytidine (1H-pyrimido [5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido [3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone.

Further nucleobases include those disclosed in U.S. Pat. No. 3,687,808, those disclosed in The Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S.T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, for example, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, each of which is herein incorporated by reference in its entirety. Further, U.S. Pat. No. 5,750,692 also teaches the preparation of certain of the above modified nucleobases and is herein incorporated by reference in its entirety.

Oligomers amendable to preparation by the methods of the invention include those having any or all of the foregoing natural or modified nucleobases. Oligomers amendable to preparation by the methods of the invention include those having one or more conjugate groups thereon, i.e., chemically linked moieties that are thought to enhance the activity, cellular distribution or cellular uptake of the oligonucleotide. The compounds of the invention can include conjugate groups covalently bound to functional groups such as primary or secondary hydroxyl groups, optionally bound through linking groups.

Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion.

Representative conjugate groups are disclosed in International Patent Application PCT/US92/09196, filed Oct. 23, 1992. Conjugate moieties include, for example, lipid moieties such as a cholesterol moiety (Letsinger et al., Proc. Natl. Acad. Sci. USA, 1989, 86, 6553–6556), cholic acid (Manoharan et al., Bioorg. Med. Chem. Let., 1994, 4, 1053–1060), a thioether, e.g., hexyl-S-tritylthiol (Manoharan et al., Ann. N.Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., Biochimie, 1993, 75, 49–54), a phospholipid, e.g., di-hexadecyl-rac-glycerol or triethylanimonium 1,2-di-O-hexadecyl-rac-glycero-3-H-phosphonate (Manoharan et al., Tetrahedron Lett., 1995, 36, 3651–3654; Shea et al., Nucl. Acids Res., 1990, 18, 3777–3783), a polyamine or a polyethylene glycol chain (Manoharan et al., Nucleosides & Nucleotides, 1995, 14, 969–973), or adamantane acetic acid (Manoharan et al., Tetrahedron Lett., 1995, 36, 3651–3654), a palmityl moiety (Mishra et al., Biochim. Biophys. Acta, 1995, 1264, 229–237), or an octadecylamine or hexylamino-carbonyl-oxycholesterol moiety (Crooke et al., J. Pharmacol. Exp. Ther., 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730 which is incorporated herein by reference in its entirety.

Representative United States patents that teach the preparation of such oligonucleotide conjugates include, for example, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941 each of which is herein incorporated by reference in its entirety.

Oligomers amendable to preparation by the methods of the invention include those having any number of modifications, including none, one, two, or more of the foregoing modifications. Indeed, it is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds may be formed using the methods of the invention as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The methods of the invention also are amenable to the preparation of other oligonucleotide mimetics where both the sugar and the internucleoside linkage, i.e., the backbone, of the nucleotide units are replaced with novel groups. In such compounds, the base units are maintained for hybridization with an appropriate nucleic acid target compound. One such oligomeric compound, an oligonucleotide mimetic that has been shown to have excellent hybridization properties, is referred to as a peptide nucleic acid (PNA).

In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone.

Representative United States patents that teach the preparation of PNA compounds include, for example, U.S. Pat. Nos. 5,539,082; 5,714,331; and 5,719,262, each of which is herein incorporated by reference in its entirety. Further teaching of PNA compounds can be found in Nielsen et al., Science, 1991, 254, 1497–1500.

The following examples, which are not intended to be limiting, present certain embodiments and advantages of the present invention.

EXAMPLES

Experiments were performed to determine the extent that filling materials reduce back pressure during solid phase synthesis processes and also to determine that solid fillers combined with a solid support could produce pressures equal to or better than system pressures when no solid support is present.

For each experiment a phosphorothioate deoxyribonucleotide 20-mer, [PS-d(5'-TCCGTCATCGCTCCTCAGGG)], was synthesized on a ACTA Oligo Pilot synthesizer, available from Amersham Pharmacia Biotech, on 1 mmol scale. In examples using a solid support, a Primer Support 200 dG was used. Standard reagents and cycles were used throughout the examples. Typical reagents include, for example, Cyanoethyl-N,N-diisopropyl phosphoramides of protected deoxyribonucleosides, tetrazole, phenylacetyl disulfide, dichloroacetic acid/toluene.

A reference solid phase synthesis was performed without filling material to determine a reference system pressure. The solid support used for the reference system was 23 ml of PRIMER 200 dG support suspended in acetonitrile and packed into the column. The flow-rate for detritylation was 92 ml/min and the flow-rate for the subsequent ACN wash was 120 ml/min. The system pressure was 7.3 bar for the detritylation and 10.2 bar for the ACN wash.

Example 1

A phosphorothioate deoxyribonucleotide 20-mer was synthesized using identical conditions as the reference system except that a filling material was mixed with the solid support. In this example glass beads from Duke Scientific ranging in size from 10–95 microns were used as filling material. The volume of glass beads equaled the volume of the solid support. The solid support and glass beads were suspended in acetonitrile, mixed thoroughly and packed into the column.

The pressures for both detritylation and acetonitrile wash were recorded at each coupling step in Table 1:

TABLE 1

|    | Reference Detritylation (Bars) | Detritylation With Filler (Bars) | Reference Wash (Bars) | Wash With Filler (Bars) |
|----|---|---|---|---|
| dG | 10.9 | 10.7 | 13.5 | 12.4 |
| dG | 11.7 | 10.2 | 13.8 | 12.5 |
| dG | 11.0 | 10.1 | 13.7 | 13.5 |
| dA | 10.8 | 11.3 | 14.0 | 13.5 |
| dC | 11.3 | 10.7 | 14.2 | 13.3 |
| T  | 10.9 | 11.0 | 14.6 | 13.1 |
| dC | 10.9 | 10.5 | 15.0 | 13.7 |
| dC | 11.2 | 10.5 | 15.5 | 13.8 |
| T  | 11.2 | 11.0 | 15.0 | 13.7 |
| dC | 11.5 | 10.5 | 15.5 | 13.7 |
| dG | 11.5 | 10.3 | 15.6 | 14.6 |
| dC | 12.1 | 10.6 | 17.6 | 14.1 |
| T  | 11.4 | 10.6 | >20  | 14.8 |
| dA | 11.2 | 10.2 | >20  | 14.6 |
| dC | 11.5 | 10.2 | 16.9 | 14.7 |
| T  | 11.6 | 10.4 | 17.9 | 155.1 |
| dG | 12.0 | 10.4 | 18.7 | 14.8 |
| dC | 12.1 | 10.8 | 17.6 | 15.6 |
| dC | 12.2 | 11.1 | 18.4 | 15.7 |
| T  |      |      |      |       |

FIG. 1 shows a graph of the pressures at each coupling. As shown in FIG. 1, the use of fill material mixed with a solid support lowers the back pressure during detritylation and the subsequent acetonitrile wash. FIG. 1 also shows that the increase in back pressure caused by the progression of oligonucleotide synthesis is reduced. Trend lines in FIG. 1 were calculated using MS EXCEL available from Microsoft Corporation. Several pressures recorded in the reference system, data points for the wash at couplings 13 and 14, exceeded the pressure maximum of 20 bars. These data points are not included in the trend line analysis.

Table 2 shows the results of the trend line analysis:

TABLE 2

|  | Reference Detritylation (Bars) | Detritylation With Filler (Bars) | Reference Wash (Bars) | Wash With Filler (Bars) |
|---|---|---|---|---|
| First Coupling | 10.9 | 10.6 | 13.2 | 12.6 |
| Last Coupling | 11.9 | 10.6 | 18.5 | 15.5 |
| Increase | 1.0 | 0.0 | 5.3 | 2.9 |

The data in Table 2 was corrected for system pressure by subtracting 7.3 bar for the detritylation step and 10.2 bar for the ACN wash. Table 3 shows the pressure obtained for the portion of the total pressure that is due to the reaction column:

TABLE 3

|  | Reference Detritylation (Bars) | Detritylation With Filler (Bars) | Reference Wash (Bars) | Wash With Filler (Bars) |
|---|---|---|---|---|
| First Coupling | 3.6 | 3.3 | 3.0 | 2.4 |
| Last Coupling | 4.6 | 3.3 | 8.3 | 5.3 |
| Increase | 1.3 | 0.0 | 5.3 | 2.9 |

The results indicate that the use of a filler reduces the pressure caused by the packing and the oligonucleotide attached to the packing while maintaining or improving the yield and quality. The yield and quality of oligonucleotides in the synthesis using filling material were comparable to the reference synthesis and within the variability typically observed. The back pressure for detritylation was lower for the reaction vessel using filling material compared to the back pressure for the reaction vessel without filling material. The back pressure for the wash was lower for the reactor using filling material compared to the back pressure for the reactor without filling material. Furthermore, using filling material reduces the pressure increase typically experienced over the course of synthesis.

Example 2

An oligomer compound having a phosphorothioate backbone, is synthesized using conventional solid phase synthesis techniques except that filling material is used as described in Example 1. Back pressure is reduced as a result of using filling material with a solid support.

Example 3

A chiral phosphorothioate is synthesized using conventional solid phase synthesis techniques except that filling material is used as described in Example 1. Back pressure is reduced as a result of using filling material with a solid support.

Example 4

A phosphotriester is synthesized using conventional solid phase synthesis techniques except that filling material is used as described in Example 1. Back pressure is reduced as a result of using filling material with a solid support.

Example 5

A aminoalkylphosphotriester is synthesized using conventional solid phase synthesis techniques except that filling material is used as described in Example 1. Back pressure is reduced as a result of using filling material with a solid support.

Example 6

A phosphoramidate, for example 3'-amino phosphoramidate or aminoalkylphosphoramidate, is synthesized using conventional solid phase synthesis techniques for phosphoramidate preparation except that filling material is used as described in Example 1. Back pressure is reduced as a result of using filling material with a solid support.

Example 7

A thionophosphoramidate is synthesized using conventional solid phase synthesis techniques for thionophosphoramidate preparation except that filling material is used as described in Example 1. Back pressure is reduced as a result of using filling material with a solid support.

Example 8

A peptide nucleic acid (PNA) is synthesized using conventional solid phase synthesis techniques except that filling material is used as described in Example 1. Back pressure is reduced as a result of using filling material with a solid support.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method comprising:
    contacting a solid support with a filling material to produce a mixture thereof, wherein the filling material is not soluble in any organic solvent or solvent mixture, or aqueous solvent or solvent mixture;
    placing the mixture in a reaction vessel suitable for solid phase synthesis; and
    synthesizing an oligonucleotide, oligonucleotide analogue, or peptide nucleic acid on the solid support.

2. The method of claim 1 wherein the filling material is glass.

3. The method of claim 1 wherein the filling material is a polymer.

4. The method of claim 1 wherein the contacting and placing steps occur simultaneously in the reaction vessel.

5. The method of claim 1 wherein the oligonucleotide is synthesized on the solid support.

6. The method of claim 1 wherein said synthesis is performed with phosphoramidite chemistry.

7. The method of claim 2 wherein the filling material is glass beads.

8. The method of claim 1 wherein the filling material is glass and the solid support is a polymer or glass beads.

9. The method of claim 1 wherein the filling material is glass beads and the solid support is glass, an aminopolyethyleneglycol derivatized support or a copolymer of polystyrene/divinylbenzene.

10. The method according to claim 1 wherein an oligonucleotide containing at least one phosphorothioate internucleoside linkage is synthesized on the solid support.

11. A reaction vessel for synthesizing oligonucleotides, oligonucleotide analogies, or peptide nucleic acids comprising: a solid support; and a filling material, wherein the filling material is not soluble in any organic solvent or solvent mixture, or aqueous solvent or solvent mixture.

12. The reaction vessel of claim 11 wherein the filling material is glass.

13. The reaction vessel of claim 12 wherein the filling material is glass beads.

14. The reaction vessel of claim 11 wherein the filling material is a polymer.

15. The reaction vessel of claim 11 wherein the filling material is glass and the solid support is a polymer or glass beads.

16. The reaction vessel of claim 11 wherein the filling material is glass beads and the solid support is glass, an aminopolyethyleneglycol derivatized support or a copolymer of polystyrene/divinylbenzene.

17. An apparatus for synthesizing oligonucleotides, oligonucleotide analogies, or peptide nucleic acids comprising a reagent source, and a reaction vessel, wherein said reaction vessel comprises a solid support and a filling material, and the filling material is not soluble in any organic solvent or solvent mixture, or aqueous solvent or solvent mixture.

18. The apparatus of claim 17 wherein the filling material is glass.

19. The apparatus of claim 18 wherein the filling material is glass beads.

20. The apparatus of claim 17 wherein the filling material is a polymer.

21. The apparatus of claim 17 wherein the filling material is glass and the solid support is a polymer or glass beads.

22. The apparatus of claim 17 wherein the filling material is glass beads and the solid support is glass, an aminopolyethyleneglycol derivatized support or a copolymer of polystyrene/divinylbenzene.

23. A composition comprising a solid support suitable for oligonucleotide synthesis and a filling material mixed therewith, wherein the filling material is not soluble in any organic solvent or solvent mixture, or aqueous solvent or solvent mixture.

24. The composition of claim 23 wherein the filling material is glass.

25. The composition of claim 24 wherein the filling material is glass beads.

26. The composition of claim 23 wherein the filling material is a polymer.

27. The composition of claim 23 wherein the filling material is glass and the solid support is a polymer or glass beads.

28. The composition of claim 23 wherein the filling material is glass beads and the solid support is glass, an aminopolyethyleneglycol derivatized support or a copolymer of polystyrene/divinylbenzene.

* * * * *

UNITED STATES PATENT AND TRADEMARK OFFICE
CERTIFICATE OF CORRECTION

PATENT NO. : 6,822,088 B2
DATED : November 23, 2004
INVENTOR(S) : Max Moore et al.

It is certified that error appears in the above-identified patent and that said Letters Patent is hereby corrected as shown below:

Title Page,
Item [56], References Cited, OTHER PUBLICATIONS, "Mayer" reference, delete "ParticleLoaded" and insert -- Particle-Loaded --;

Column 15,
Lines 7 and 25, delete "analogies" and insert -- analogues --.

Signed and Sealed this

Sixth Day of June, 2006

JON W. DUDAS
*Director of the United States Patent and Trademark Office*